United States Patent
Sarkar et al.

(10) Patent No.: US 11,654,420 B2
(45) Date of Patent: May 23, 2023

(54) PROCESS AND CATALYST FOR LOW TEMPERATURE NON-OXIDATIVE DEHYDROGENATION OF PROPANE TO PROPYLENE

(71) Applicant: Council of Scientific & Industrial Research, New Delhi (IN)

(72) Inventors: Bipul Sarkar, Dehradun (IN); Ankit Agrawal, Dehradun (IN); Om Vir Singh, Dehradun (IN); Indrajit Kumar Ghosh, Dehradun (IN); Shailendra Tripathi, Dehradun (IN); Sanat Kumar, Dehradun (IN); Anjan Ray, Dehradun (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 17/365,504

(22) Filed: Jul. 1, 2021

(65) Prior Publication Data
US 2022/0001359 A1    Jan. 6, 2022

(30) Foreign Application Priority Data

Jul. 3, 2020    (IN) .............................. 202011028344

(51) Int. Cl.
*B01J 23/28* (2006.01)
*B01J 23/08* (2006.01)
(Continued)

(52) U.S. Cl.
CPC .............. *B01J 23/28* (2013.01); *B01J 29/16* (2013.01); *B01J 29/48* (2013.01); *B01J 35/10* (2013.01);
(Continued)

(58) Field of Classification Search
CPC ............ B01J 23/08; B01J 23/14; B01J 23/28; B01J 29/16; B01J 29/48; B01J 35/002;
(Continued)

(56) References Cited

U.S. PATENT DOCUMENTS 4,130,507 A * 12/1978 Hayes .................... C07C 5/3337
502/220
4,976,847 A * 12/1990 Maxwell ................. B01J 29/005
208/120.35
(Continued)

FOREIGN PATENT DOCUMENTS

| WO | 199523123 A1 | 8/1995 |
| WO | 2007018982 A1 | 2/2007 |
| WO | 2014016811 A1 | 1/2014 |

OTHER PUBLICATIONS

Duan, et al., "Effect of Sodium Addition to PtSn/AISBA-15 on the Catalytic properties in propane Dehydrogenation", Catal Lett., vol. 141, pp. 120-127, 2011.
(Continued)

*Primary Examiner* — In Suk C Bullock
*Assistant Examiner* — Jason Y Chong
(74) *Attorney, Agent, or Firm* — Dinsmore & Shohl, LLP (57) ABSTRACT

A process and catalyst are provided for the non-oxidative dehydrogenation of propane for the production of propylene as petrochemical building blocks. The process provides a direct single-step gas-phase dehydration of propane mixed with nitrogen in the presence and absence of steam/hydrogen over supported bimetallic alumina-silicates zeolites. The catalyst contains no precious metal entities and may contain one metal from group VIB in combination with another metal from group IIIA or IVA supported on FAU, MFI, KFI, BEA type alumina-silicates zeolites. The process provides a propane conversion of 18% to 52% with a propylene yield of 10% to 25%.

18 Claims, 3 Drawing Sheets

(51) Int. Cl.
- *B01J 23/14* (2006.01)
- *B01J 29/16* (2006.01)
- *B01J 29/48* (2006.01)
- *B01J 35/10* (2006.01)
- *B01J 37/04* (2006.01)
- *B01J 37/08* (2006.01)
- *C07C 5/333* (2006.01)
- *B01J 37/00* (2006.01)
- *B01J 37/02* (2006.01)

(52) U.S. Cl.
CPC ....... *B01J 37/0045* (2013.01); *B01J 37/0201* (2013.01); *B01J 37/04* (2013.01); *B01J 37/08* (2013.01); *C07C 5/3335* (2013.01); *B01J 23/08* (2013.01); *B01J 23/14* (2013.01); *B01J 2229/186* (2013.01); *C07C 2523/28* (2013.01); *C07C 2529/16* (2013.01); *C07C 2529/48* (2013.01)

(58) Field of Classification Search
CPC .... B01J 35/10; B01J 37/0045; B01J 37/0201; B01J 37/04; B01J 37/08; B01J 2229/186; C07C 5/333; C07C 5/3335; C07C 2523/28; C07C 2529/16; C07C 2529/48; C07C 2529/58; Y02P 20/52

See application file for complete search history.

(56) References Cited

U.S. PATENT DOCUMENTS

| | | |
|---|---|---|
| 5,073,662 A | 12/1991 | Olbrich |
| 5,151,401 A | 9/1992 | Schubert et al. |
| 2015/0202599 A1* | 7/2015 | Al-Zahrani ............. B01J 23/36 502/329 |
| 2020/0070128 A1* | 3/2020 | Suriye .................... B01J 23/626 |

OTHER PUBLICATIONS

Li, et al., "Size effect of TS-1 supports on the catalytic performance of PtSn/TS-1 catalysts for propane dehydrogenation", Journal of Catalysis, vol. 352, pp. 361-370, 2017.

\* cited by examiner

PROCESS AND CATALYST FOR LOW TEMPERATURE NON-OXIDATIVE DEHYDROGENATION OF PROPANE TO PROPYLENE

CROSS-REFERENCES TO RELATED APPLICATIONS

This application claims the benefit of priority under 35 U.S.C. § 119 to Indian Patent Application No. 202011028344, filed Jul. 3, 2020, which application is incorporated herein by reference in its entirety.

TECHNICAL FIELD

The present invention related to a process and a catalyst for the dehydrogenation of propane for the production of propylene as petrochemical building blocks. Particularly the present invention relates to a catalyst excluding novel metals from group VIIB for the production of propylene in a continuous fixed bed reactor system under atmospheric pressure. More particularly, the present invention relates to a low-temperature process to produce propylene over alumina-silicate zeolites. The present invention relates to an improved process for the preparation of supported bimetallic alumina-silicate zeolites (FAU, MFI, KFI, BEA etc.); the catalyst may contain one metal from group VIB in combination with another metal from group IIIA or IVA. The catalyst can offer propylene without any deactivation in a longer run.

BACKGROUND

In the petrochemical industry, the small chemicals primarily ethylene and propylene are very important. High valued chemicals such as ethylene oxide, polyethylene, propylene oxide, polypropylene, acrylonitrile, cumene etc. are synthesized by those small building blocks. Traditionally, in refineries, the propylene is produced by steam cracking and fluid catalytic cracking from the naphtha and other feedstocks. Due to an increase in demand for propylene in petrochemical and other sectors, these ways are not enough to feed them. So, in the USA and China, the shale gas reservoirs are being searched as the natural gas resources. As these reservoirs are the rich source of ethane and propane and the higher price gap in between their respective olefins, dehydrogenation and oxidative dehydrogenation are regarded as another way of production.

Dehydrogenation is an endothermic reaction that requires the high temperature and the mild pressure to obtain the high yield of propylene when propane is used as feedstock. High temperature favors the high yield but also leads to the high coke deposition on the catalyst surface hence the catalyst deactivation happens rapidly. Many efforts have been done to maintain stability, activity and other important aspects. Technology giants like UOP and Lummus have commercially offered catalyst and process solutions for the continuous production of propylene. The traditional catalysts employed are platinum (Pt) and $CrO_x$ based, while the former one is precious, later one is poisonous in nature. However, these catalysts are prone to deactivate in a very short time. So, extensive investigations have been done to find suitable catalysts over the recent years experimentally and theoretically. Various novel metals with the zeolite support system such as Zinc (Zn), Tin (Sn), Gallium (Ga), Cobalt (Co) and carbon-based material have been reported for catalyzing propane dehydrogenation (PDH) and oxidative dehydrogenation of propane (ODH) which are void of shortcomings typical of commercial $CrO_x$ and Pt-based catalysts.

A few studies have also been done on molybdenum-based catalysts. Mo-based catalysts have been frequently used for the hydrocarbon conversion reaction including dehydrogenation reactions. The first report of the dehydrogenation activity of a molybdenum oxide-based catalyst was of $MoO_3/Al_2O_3$ in the dehydrocyclization of n-heptane, which was published in 1946. Since the first report, the study on Mo-based catalysts was done seldom, as emphasis has been given to the study of oxidative dehydrogenation on these materials. Therefore, the development of a robust Mo composite catalyst with a blend of admirable activity, stability, and good resistance to coke and sintering is highly desirable from both an academic and industrial viewpoint.

Reference can be made to the WO patent WO1995023123A1 by ABB Lummus Crest Inc. wherein R. J. Gartside et al. explored an endothermic dehydrogenation process of hydrocarbon feed over $CrOx/Al_2O_3$ catalyst with the alkali promoter for the production of propylene. Adiabatic fixed bed was used at 565-649° C. to achieve 48-65% $C_3$ conversion. Propylene was obtained with 80-88% selectivity at 0.3-0.5 bar pressure but the catalyst cycle time is very low. Additionally, the poisonous nature of Cr is also a matter of concern.

Reference can be made to the WO patent WO2007018982A1 filled by Sud-Chemie Inc. on an adiabatic, non-oxidative dehydrogenation of hydrocarbons. In the patent, V. Fridman and his co-worker describe a catalyst bed that includes a first layer of a catalyst and second layer of a catalyst. The hydrocarbon feed first contacts the catalysts of the first layer, wherein the catalysts of each layer exhibit different, predetermined capacities for the production of coke. Moreover, the catalyst deactivates fast as only 20h time-on-steam was detailed. The catalyst consists of 70 to 90% by weight alumina and from 10 to 30% by weight one or more chromium compounds. Such a high concentration of poisonous Cr was used to achieve the production of propylene.

Reference can also be made to the WO patent WO2013089859A1 by UOP LLC. detailing a hydrocarbon dehydrogenation process using an inert diluent over Pt—Sn on $Al_2O_3$ with an alkali promoter. A propane conversion of about 25% with propylene selectivity of 91% was achieved at 2-3 bar pressure. The high cost of Pt makes the CAPEX high for the process and the temperature (550-620° C.) of the process is relatively high.

Reference can also be made to the US patents U.S. Pat. Nos. 5,151,401A and 5,073,662A by Phillips Petroleum Company, detailing the preparation of supported platinum catalysts for the dehydrogenation of propane to propylene. The catalyst comprises Pt and Sn over a mixture of $ZnAl_2O_3$ and $CaAl_2O_3$; where the amount of Pt may vary 0.3-0.6 wt % over porous support contains about 89.6 wt % zinc aluminate, about 9.1 wt % calcium aluminate and about 1.3 wt % stannic oxide. Over 40% propane conversion was noted with 89% propylene selectivity at 550-590° C. But the reaction pressure is high (5-6 bar) compare to others with the use of noble metal.

Reference can also be made to the WO patent WO2014016811A1 by Sabic Innovative Plastics Ip. for an alkane dehydrogenation catalyst comprising a precious metal e.g., Pt, Pd, Rh, Ir with Sn or Zn over porous SAPO-34. A propane conversion of 48-65% with propylene selectivity of 88-93% was achieved at 0.1-6 bar pressure. The reaction temperature is very high (560-600° C.) and the catalyst is costly as it contains Pt. Moreover, the catalyst cycle time is very short (15-30 minute) and hence required a rapid regeneration protocol.

Reference can be made to the Journal of Catalysis 352, 2017, 361-370 wherein Li et al. reported a PtSn/TS-1 catalyst for propane dehydrogenation. At optimal condition, 48% propane conversion was observed with 95% propylene selectivity but relatively high temperature used (590° C.) and catalyst also shows deactivation via coke formation within $8^{th}$ h of reaction.

Reference may also be made to Catalysis Letters 141, 2011, 120-127 in which effect of the effect of sodium been assessed on PtSn/AlSBA-15 catalysts for the production of propylene. A propane conversion of >12% was achieved with 94% propylene selectivity at 590° C. But the main drawback is low propane conversion and rapid deactivation cause by prompt agglomeration and coking during the reforming process.

The present disclosure relates to the synthesis of non-noble catalyst for the propane dehydrogenation reaction for the continuous production of propylene at low temperature with high propylene selectivity.

The main object of the present disclosure is to provide a catalyst for the low-temperature dehydrogenation of propane to propylene with high propylene selectivity.

Another object of the present disclosure is to provide a bi-metallic catalyst free from noble metal entity with one metal selected from group VI-B in combination with another metal selected from group III-A or IV-A.

Yet another object of the present disclosure is to provide a process that selectively gives propylene via propane dehydrogenation, with a 10-16% propane diluted with nitrogen in the presence or absence of molecular hydrogen/steam.

Yet another object of the present disclosure is to provide a continuous process and noble metal-free catalyst for low-temperature production of propylene.

Yet another object of the present disclosure is to provide a process that works continuously more than 20 hours without any major deactivation of the catalyst under continuous process for the production of propylene from propane.

Yet another object of the present disclosure is to provide a bimetallic catalyst consisting of one metal from group VIB in combination with another metal from group IIIA or IVA and which can be prepared easily and also very economical to produce propylene.

SUMMARY

In one embodiment, the present disclosure relates to a catalyst composition comprising: (a) a porous alumina-silicate zeolite Faujasite (FAU), Zeolite Mobil type Five (MFI), Zeolite Kerr Five (KFI), Zeolite Beta polymorph A (BEA), etc. as catalyst support; (b) a first metal is a transition metal of group VIB, wherein the amount of the first metal is in the range of between 1 to 10 wt % based on the porous zeolite support; (c) a second metal is selected from a group IIIA or IVA, wherein the amount of the second metal is in the range of between 1 to 8 wt % based on the catalyst support; and (d) an alkali metal, wherein the amount of alkali metal is in the range of 0.5 to 2 wt % based on the catalyst support.

In another embodiment, the transition metal is selected from the group consisting of Molybdenum (Mo), chromium (Cr), and tungsten (W).

In another embodiment, the second metal is selected from the group consisting of tin (Sn), gallium (Ga), and Indium (In).

Further, in another embodiment, the alkali metal is selected from the group consisting of Sodium (Na), potassium (K), and cesium (Cs).

In another embodiment, a process for the preparation of the catalyst composition, the process comprising the steps of: (a) depositing a first metal selected from transition metal of group VIB, a second metal selected from a group IIIA or IVA, and an alkali metal on a porous alumina-silicate zeolite support to obtain a catalyst precursor; and (b) exposing the catalyst precursor of step (a) for calcination in an environment comprising air or nitrogen to obtain a catalyst; wherein the porous alumina-silicate zeolite support is selected from the group consisting of FAU, MFI, KFI and BEA.

Further, in another embodiment, the transition metal used in step (a) is selected from the group consisting of Molybdenum (Mo), chromium (Cr), and tungsten (W).

In another embodiment, the second metal used in step (a) is selected from the group consisting of tin (Sn), gallium (Ga), and Indium (In).

In another embodiment, the alkali metal used in step (a) is selected from the group consisting of Sodium (Na), potassium (K), and cesium (Cs).

Further, in another embodiment, a process for the preparation of the catalyst precursor as obtained in step (a), the process comprising the steps of: (a) dissolving an ammonium, nitrate and chloride salt of either one of the first metal selected from transition metal of group VIB in water; wherein the transition metal is selected from the group consisting of Molybdenum (Mo), chromium (Cr), and tungsten (W); (b) dissolving a nitrate and chloride salt of either one of the second metal selected from group IIIA or IVA in water; the second metal is selected from the group consisting of tin (Sn), gallium (Ga) and Indium (In); (c) mixing both solutions of step (a) and (b) followed by addition of cetyl trimethylammonium bromide (CTAB) in an amount of first and/or second metal(s) to CTAB ratio of 1:0.1 to 1:10 and kept for aging for the time period in the range of 1 to 2 h; (d) adding the porous alumina-silicate zeolite in the form of powder during aging of step (c) to obtain a white slurry; wherein a temperature of the white slurry containing CTAB, zeolite, metal, and alkali metal is in the range of between 40-90° C.; (e) homogenizing the white slurry of step (d) followed by drying in an oven at a temperature in the range of 100 to 150° C. for the time period in the range of 10 to 18 h to obtain a material; and (f) calcining the material as obtained in step (e) at a temperature in the range of 300 to 800° C. for the time period in the range of 4 to 6 h in the air to obtain the catalyst precursor as claimed in claim 4, step (a).

Furthermore, in another embodiment, a continuous process for low temperature non-oxidative dehydrogenation of propane to propylene using the catalyst composition, the process comprising the steps of: (a) passing a mixture of propane and helium in the absence or presence of hydrogen (1-5%) or steam (1-5%) in a ratio of 4:20 in a reactor; wherein the reactor is kept at a pressure in the range of 0.9-5 bar, a temperature in the range of 350-700° C. with a gas hourly space velocity (GHSV) in the range of 5000-9000 $h^{-1}$ over the catalyst composition for a reaction period in the range of between 1-24 hours to obtain a reaction product predominated with the propylene.

In another embodiment, the process step (a) of presence of hydrogen or steam is to create partial pressure difference in between upper part (Feed) and lower part (product) of the reactor. According to the Le Chatelier's principle where pressure is low, the equilibrium shift towards that direction.

In another embodiment, the continuous process gives a reaction product with side products selected from methane, ethane, ethylene, or combination thereof.

Further, in another embodiment, the continuous process provides conversion of the propane to propylene in the range of 18-52% at a temperature of 450° C.

Furthermore, in another embodiment, the continuous process gives a yield of the propylene in the range of 10-25%.

ABBREVIATIONS USED IN THIS DISCLOSURE

FAU: Faujasite
MFI: Zeolite Mobil type Five
KFI: Zeolite Kerr Five
BEA: Zeolite Beta polymorph A
PDH: propane dehydrogenation
ODH: oxidative dehydrogenation of propane
Mo: Molybdenum
Zn: Zinc
Pt: Platinum
Cr: chromium
W: tungsten
Sn: tin
Ga: gallium
In: Indium
Pd: Palladium
Rh: Rhodium
Ir: Iridium
SAPO-34: Silicoaluminophosphate-34 Zeolite
TS-1: Titanosilicate-1
A1SBA-15: Aluminium-Santa Barbara Amorphous-15
GHSV: gas hourly space velocity
CTAB: cetyl trimethylammonium bromide
XRD: X-ray Diffraction
TEM: Transmission Electron Microscope

DETAILED DESCRIPTION

The present disclosure provides a catalyst consisting of a transition metal selected from group VIB, comprising one of Molybdenum (Mo), chromium (Cr), and tungsten (W), and a second metal from group IIIA or IVA, comprising one of tin (Sn), gallium (Ga), and Indium (In) on porous alumina-silicate zeolite like FAU, MFI, KFI, BEA, etc. The amount of transition metal selected from group VIB is kept between 1 to 10 wt % based on the porous zeolite support and the amount of second metal selected from group IIIA or IVA was kept between 1% to 8%. The catalyst was prepared by wetness impregnation as well as template-assisted (CTAB) wetness impregnation method for low-temperature non-oxidative dehydrogenation of propane. The process pressure was kept between 0.9-5 bar, at a temperature range of 350 to 700° C. with a gas hourly space velocity (GHSV) in the range of 5000-9000 $h^{-1}$. The catalyst was found stable for a period of 12-24 h time-on-steam.

The present disclosure relates to the synthesis of Mo—Sn-FAU catalyst as described above for the non-oxidative dehydrogenation of propane for the production of propylene which involves the following steps:

i. Synthesizing molybdenum impregnated faujasite using molybdenum precursor and CTAB;

ii. heating the Molybdenum impregnated faujasite at 50° C. and maintained for 1-2 h;

iii. filtering the material obtained in step ii by washing with excess water and ethanol (1 liter) followed by drying the material in the oven at a temperature between 100-130° C. for 10-18 h;

iv. Calcining the material of step ii at a temperature of 500° C. for a time period of 4-6 h in the air to get solid Mo-FAU;

v. Synthesizing Mo—Sn-FAU catalyst using tin chloride (Sigma-Aldrich, >99%) as a source of Sn, which is dissolved in water and heated at a temperature of 50° C.;

vi. The weight ratio of Mo to faujasite was kept in the range of 2 to 8%; The weight ratio of Sn to faujasite was kept in the range of 3 to 5%; after homogenizing, the mixture of step v was heated further at a temperature of 60° C. and stirred for 1 h.

vii. Adding 5-10 g of previously prepared nanoporous Mo-FAU zeolite in step vi material and kept at stirring for 1-2 h at the same temperature to obtain precipitate.

viii. The precipitate of step vii was cooled down to room temperature naturally, collected and washed with ethanol and water several times;

ix. Calcining the material of step viii at a temperature of 500° C. for a time period of 4-6 h in the air to get Mo—Sn-FAU catalyst;

x. Thereafter, a Non-oxidative dehydrogenation of propane was carried out in a fixed bed down-flow reactor using $C_3H_8:N_2$ in 1:5 ratio in the presence of Mo—Sn-FAU catalyst for 1-24 h to get propylene;

xi. The reaction parameters of step x like pressure was kept at 1 atmosphere;

temperature is preferably in the range 250 to 550° C.; The gas hourly space velocity (GHSV in ml $g^{-1}h^{-1}$) is preferably in the range 5000 ml $g^{-1}h^{-1}$ to 9000 ml $g^{-1}$ $h^{-1}$;

The propane conversion (mol %) of 30-50% and propylene selectivity of 40-50% with ratio of $C_3H_8:N_2$ in 1:5 (mol %).

The present disclosure is also related to the synthesis of Mo—Ga-MFI catalyst as described above for the non-oxidative dehydrogenation of propane for the production of propylene which involves the following steps:

i. Synthesizing of Molybdenum impregnated MFI using of molybdenum precursor, and CTAB;

ii. heating the Molybdenum impregnated MFI at 50° C. and maintained for 1 hour to 2 hours;

iii. filtering the material obtained in step ii by washing with excess water and ethanol (1 liter) followed by drying the materials in the oven at a temperature from 100° C. to 130° C. for 10 hours to 18 hours;

iv. Calcining the materials of step iii at a temperature of 500° C. for a time period of 4-6 h in the air to get solid Mo-MFI;

v. Synthesizing of Mo—Ga-MFI catalyst using gallium nitrate (Sigma-Aldrich, >99%) as a source of Ga, which is dissolved in water heated at a temperature of 50° C.;

vi. The weight ratio of Mo to MFI was kept in the range of 2 to 8%;

vii. The weight ratio of Ga to MFI was kept in the range of 3 to 5%;

viii. After homogenization, the mixture was heated further to a temperature of 60° C. and stirred for 1 h.

ix. Adding 5-10 g of previously prepared nanoporous Mo-MFI zeolite in step viii materials and kept at starring for 1-2 h at the same temperature to obtain precipitate.

x. The precipitate of step ix was cooled down to room temperature naturally, collected and washed with ethanol and water several times;

xi. Calcining of the materials of step x at a temperature of 500° C. for a time period of 4-6 h in the air to get catalyst Mo—Ga-MFI;

xii. Thereafter a dehydrogenation of propane was carried out in a fixed bed down-flow reactor using $C_3H_8:N_2$ in 1:5 ratio in presence of Mo—Ga-MFI catalyst for 1-24 h to get propylene;

xiii. The reaction parameters like pressure was kept at 1 atmosphere; the reaction temperature is preferably in the range 250 to 550° C.; the gas hourly space velocity (GHSV in ml $g^{-1}h^{-1}$) is preferably in the range 5000 ml $g^{-1}h^{-1}$ to 9000 ml $g^{-1}$ $h^{-1}$;

The propane conversion (mol %) of 25-45% and propylene selectivity of 45-60% with ratio of $C_3H_8:N_2$ in 1:5 (mol %).

The present invention is also related to the synthesis of K—Mo—Sn-MFI catalyst as described above for the non-oxidative dehydrogenation of propane for the production of propylene which involves the following steps:

i. Synthesizing potassium loaded MFI zeolite using potassium precursor;

ii. Mixing the potassium loaded MFI zeolite homogeneously and maintained for 2-3 h;

iii. Filtering the materials obtained in step ii with excess water and ethanol and dried the material in the oven at a temperature of 100-150° C. for overnight;

iv. Calcining the synthesized materials of step iii at a temperature of 450° C. for a time period of 4-6 h in the air to get K-MFI;

v. Synthesizing Molybdenum impregnated K-MFI catalyst using of potassium precursor, and CTAB;

vi. Heating the materials obtained in step v at a temperature of 50° C. and maintained for a time period of 1-2 h;

vii. filtering the materials obtained in step vi by washing with excess water and ethanol (1 liter) followed by drying the materials in the oven at a temperature between 100-130° C. for a time period of 10-18 h;

viii. Calcining the materials obtained in step vii at a temperature of at 500° C. for a time period of 4-6 h in the air to get solid K—Mo-MFI;

ix. Synthesizing K—Mo—Sn-MFI catalyst using ammonium molybdate (Sigma-Aldrich, >99%) and tin chloride (Sigma-Aldrich, >99%) as a source of Mo and Sn, which is dissolved in water heated at a temperature of 50° C.;

x. The weight ratio of K to MFI was kept in the range of 0.5 to 2%;

xi. The weight ratio of Mo to MFI was kept in the range of 2 to 8%;

xii. The weight ratio of Sn to MFI was kept in the range of 3 to 5%;

xiii. After homogenization, the mixture was heated further to a temperature of 60° C. and stirred for 1 hour.

xiv. Adding a 5-10 g of previously prepared nanoporous K-MFI zeolite of step xiii materials and kept at starring for 1-2 h at the same temperature to obtain a precipitate.

xv. The precipitate obtained in step xiv was cooled down to room temperature naturally, collected and washed with ethanol and water several times;

xvi. Calcining the materials as obtained in step xv at heated a temperature of 500° C. for a time period of 4-6 h in the air to get K—Mo—Sn-MFI catalyst;

xvii. Thereafter, a dehydrogenation of propane was carried out in a fixed bed down-flow reactor using $C_3H_8:N_2$ in 1:5 ratio in the presence of K—Mo—Sn-MFI for 1-24 h to get propylene;

xviii. The reaction parameters like pressure was kept at 1 atmosphere; the reaction temperature is preferably in the range 250 to 550° C.; the gas hourly space velocity (GHSV in ml $g^{-1}$ $h^{-1}$) is preferably in the range 5000 mL $g^{-1}h^{-1}$ to 9000 mL $g^{-1}h^{-1}$;

The propane conversion (mol %) of 35-45% and propylene selectivity of 50-55% with ratio of $C_3H_8:N_2$ in 1:5 (mol %).

EXAMPLES

The following examples are given by way of illustration, therefore, should not be construed to limit the scope of this disclosure or the appended claims.

Example 1

Synthesis of Metal-Doped Alumina Silicate

All the catalysts were synthesized by the incipient wet-impregnation method. The support alumina-silicate were selected from FAU, MFI, KFI, BEA; as they offer different pore networks, surface area, etc. Metals were impregnated on the above-mentioned support in a predefined manner. The concentration of metals was decided based on the already available industrial catalysts.

Synthesis of Molybdenum Impregnated Alumina-Silicate Zeolites

The synthesis of Mo-FAU was carried out by a template-assisted wetness impregnation method. The amount of molybdenum was doped on the surface was kept at 6%. It was synthesized by taking a calculated amount of molybdenum salt and it was dissolved in a sufficient amount of water. During stirring 10 g of each faujasite and MFI zeolite were added slowly into the different vessels. The whole solution was allowed to stir for 1-3 h to ensure the homogeneity of the mixture. Then, the solution was kept in the oven overnight at 50° C. Then the solution was filtered using grade 1, 2.5 μm Whatman filter paper and washed with water and ethanol. Finally, the calcination of the material was carried out at 500° C. for 4 h in air with a slow ramp rate.

Figure 1:
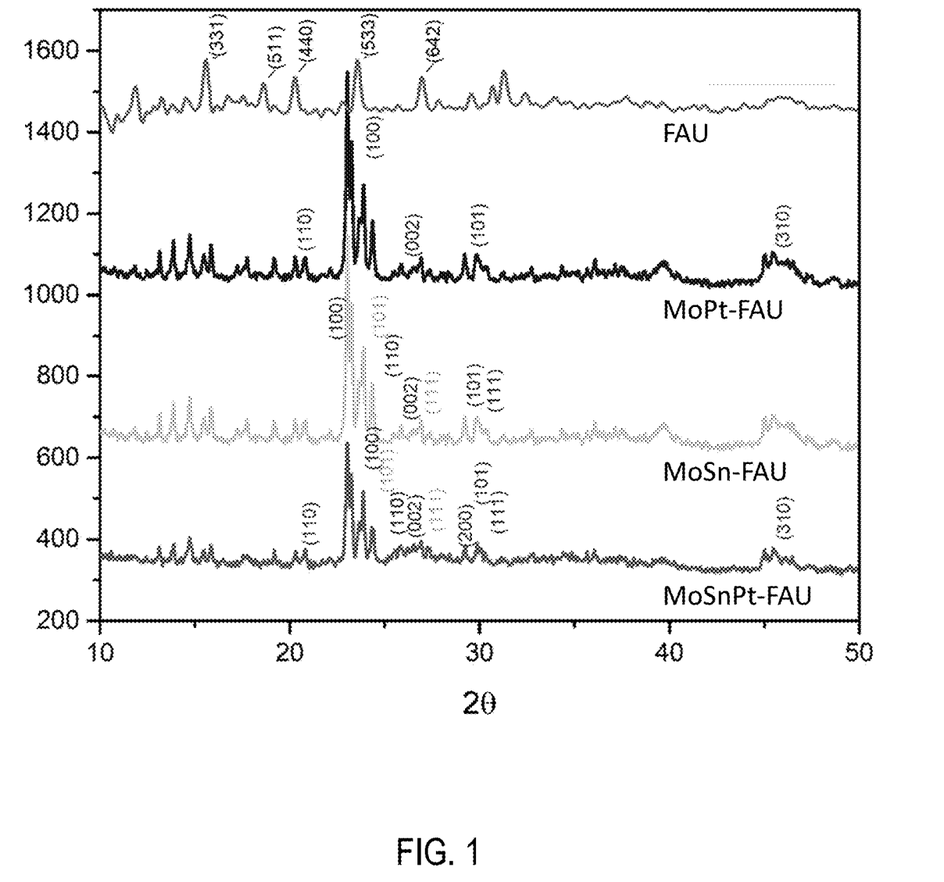
FIG. 1 represents the X-ray Diffraction (XRD) pattern of the prepared catalyst.
Figure 2:
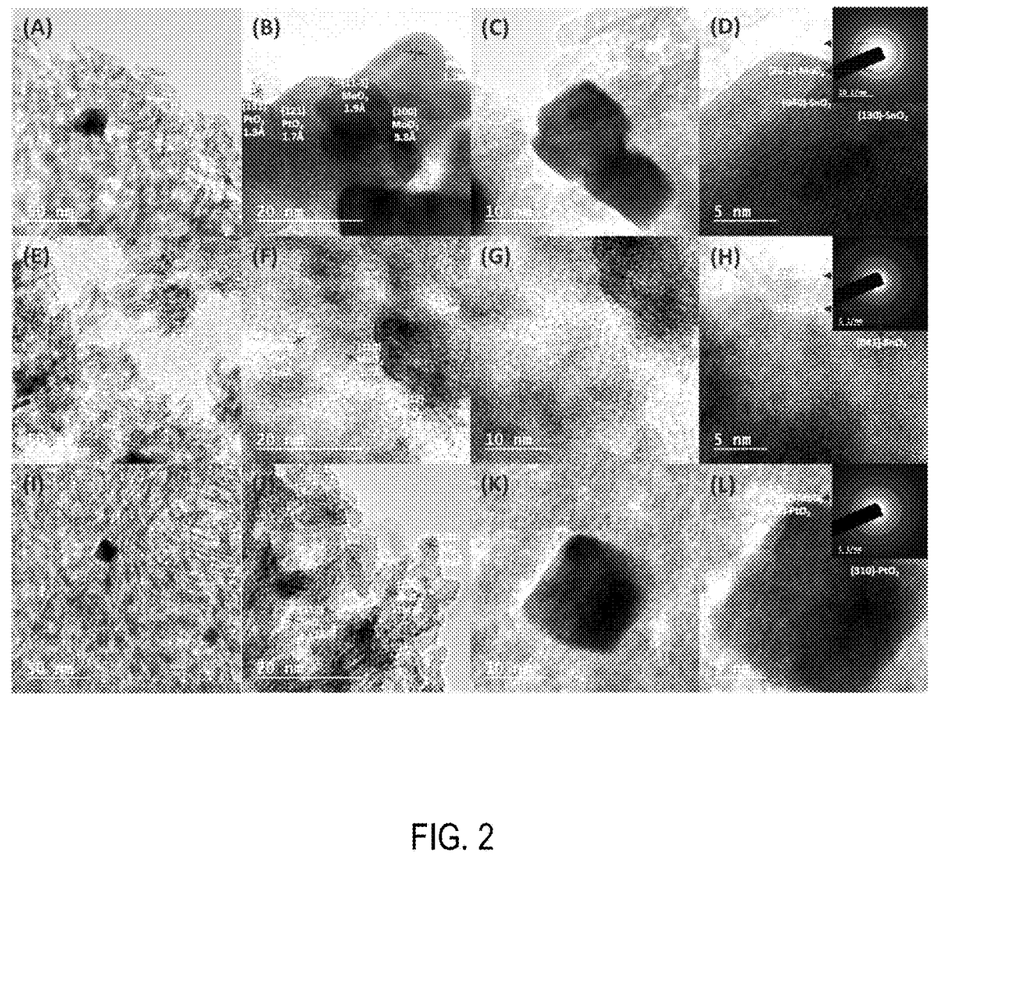
FIG. 2 represents the Transmission Electron Microscope (TEM) images of the prepared catalyst.
Figure 3:
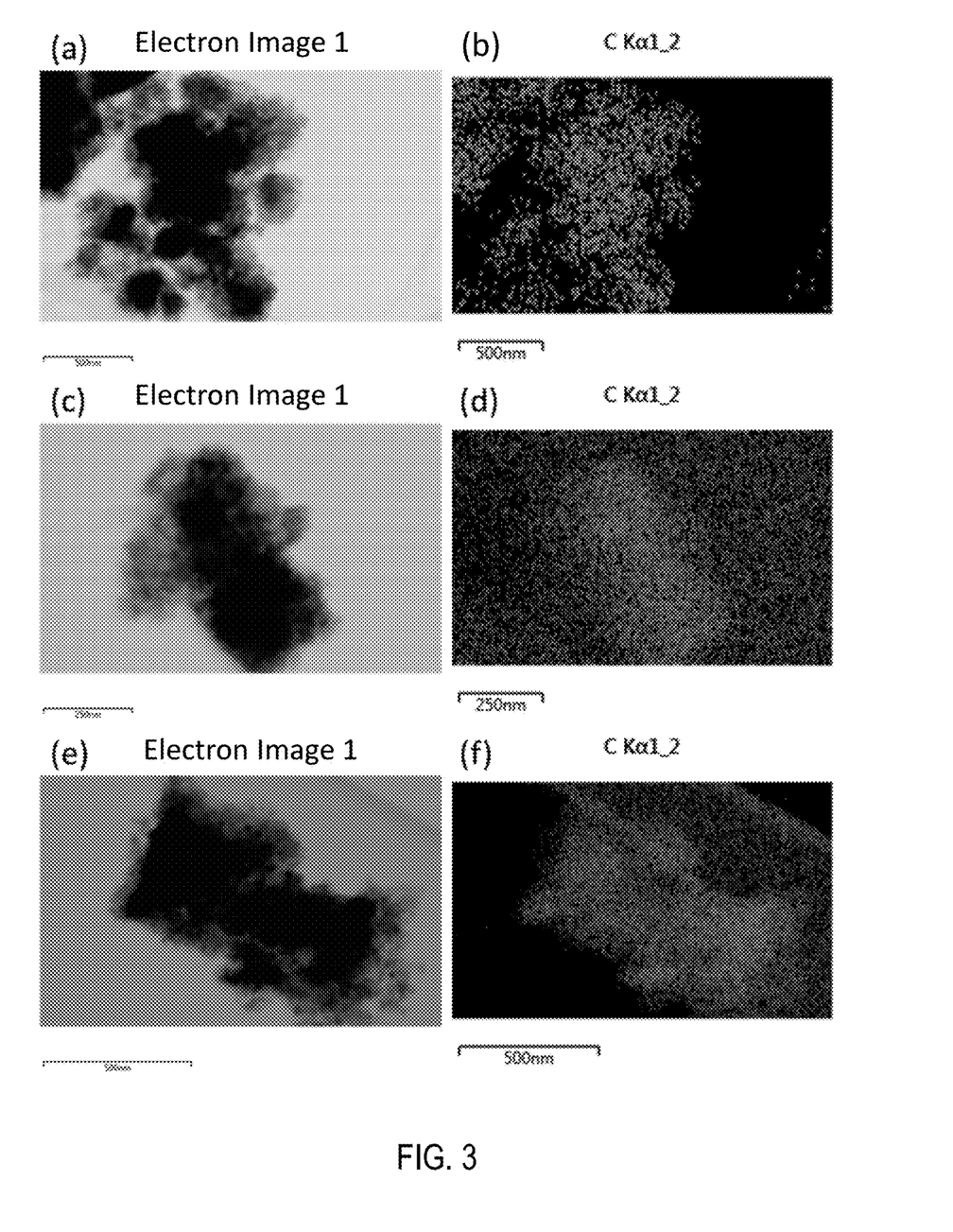
FIG. 3 represents the carbon elemental mapping of the prepared catalyst.

The X-ray powder diffraction pattern and Transmission Electron Microscope (TEM) images of this material are given below.

Example 2

Synthesis of Sn Impregnated Mo-FAU Zeolites

Synthesis of Mo—Sn-FAU was carried out by a template-assisted wetness impregnation method. The amount of tin was doped on the surface was kept at 4%. The above-mentioned zeolite was synthesized by taking the known amount of tin salt and it was dissolved in a sufficient amount of water. During stirring 2 g previously prepared Mo-FAU zeolite was added slowly. The whole solution was allowed to stir for 1-3 h to ensure the homogeneity of the mixture. Then the solution was kept in the oven overnight at 50° C. Then the solution was filtered using grade 1, 2.5 μm Whatman filter paper and washed with water and ethanol. Finally, the calcination of the material was carried out at 500° C. for 4 h in air with a slow ramp rate.

Example 3

Synthesis of Ga Impregnated Mo-MFI Zeolites

Synthesis of Mo—Ga-MFI was carried out by a template-assisted wetness impregnation method. The amount of Ga was doped on the surface was kept at 4%. The above-mentioned zeolite was synthesized by taking the known amount of gallium salt and it was dissolved in a sufficient amount of water. During stirring 2 g previously prepared Mo-MFI zeolite was added slowly. The whole solution was allowed to stir for some more time to ensure the homogeneity of the mixture. Then, the solution was kept in the oven overnight at 50° C. Then the solution was filtered using grade 1, 2.5 µm Whatman filter paper and washed with water and ethanol. Finally, the calcination of the material was carried out at 500° C. for 4 h in air with a slow ramp rate.

TABLE 1

| Catalyst | Weight of Pt-salt (mg) | Weight of Sn/Ga-salt (mg) | Weight of CTAB (mg) |
|---|---|---|---|
| Sn—Mo-FAU | — | 300-500 | 500 |
| Ga—Mo-MFI | — | 500-600 | 500 |

Example 4

This example describes the propane dehydrogenation by gas phase reaction with $C_3H_8:N_2$ mole ratio 1:5 using all the synthesised nanocrystalline zeolites as the catalysts. (Table 2)

The dehydrogenation of propane was carried out in a fixed-bed, down flow quartz reactor at atmospheric pressure. Typically, 200 mg of said synthesized catalyst (as provided in Examples 2 and 3 of this disclosure) was placed in between Silicon carbide with one quartz wool plugged at the bottom of the 8 mm quartz reactor, and dehydrogenation of methane was carried out in a temperature range of 250-550° C. The gas hourly space velocity (GHSV) was varied between 3000 mL $g^{-1}h^{-1}$ to 10000 mL $g^{-1}h^{-1}$ with a molar ratio of $C_3H_8:N_2$ of 1:5.

Process Conditions
Catalyst: 0.2 g
Mo—Sn-FAU wt % in the catalyst=6% of Mo and 4% of Sn
Pressure: 1 atmosphere
Total flow=25 mL/min (GHSV=7200)
Reaction time: 3 h
Molar ratio of $C_3H_8/N_2$: 1:5.

TABLE 2

| Catalyst | Temperature (° C.) | Propane Conversion (mol %) * | Propylene Selectivity (mol %) † | $C_3H_8/N_2$ (mol %) |
|---|---|---|---|---|
| Mo—Sn-FAU | 450 | 45 | 50 | 1:5 |

* X, † Y: The conversion and selectivity were taken as the base in subsequent tables.

Example 5

The present example describes the effect of different temperature values on propane conversion. The product analysis is presented in Table 3.

Process Conditions:
Catalyst: 0.2 g
Mo—Ga-MFI wt % in the catalyst=6% of Mo and 4% of Ga
Pressure: 1 atmosphere
Total flow=25 mL/min (GHSV=7200)
Reaction time: 3 h
Molar ratio of $C_3H_8/N_2$: 1:5

TABLE 3

| | Temperature (° C.) | Propane Conversion (mol %) | Propylene Selectivity (mol %) | $C_3H_8/N_2$ (mol %) |
|---|---|---|---|---|
| Dehydrogenation of propane to propylene | 300 | X − 20 | Y − 20 | 1:5 |
| | 400 | X − 12 | Y − 10 | 1:5 |
| | 450 | X − 5 | Y − 5 | 1:5 |
| | 500 | X + 2 | Y + 10 | 1:5 |
| | 550 | X + 10 | Y + 15 | 1:5 |

X = 45% and Y = 50%

Here, X is % conversion of propane dehydrogenation to propylene using Mo—Sn/FAU catalyst and Y is % selectivity of propane dehydrogenation to propylene using Mo—Sn/FAU catalyst.

Example 6

The example describes the effect of time on stream on propane conversion. The product analysis presented in Table 4.

Process Conditions:
Catalyst: 0.2 g
Mo—Sn-FAU wt % in the catalyst=6% of Mo and 4% of Sn
Pressure: 1 atmosphere
Total flow=25 ml/min (GHSV=7200)
Reaction time: 22 h
Molar ratio of $C_3H_8/N_2$: 1:5.

TABLE 4

| | Time (mins) | Propane Conversion (mol %) | Propylene Selectivity (mol %) | $C_3H_8/N_2$ (mol %) |
|---|---|---|---|---|
| Dehydrogenation of propane to propylene | 240 | X − 25 | Y + 2 | 1:5 |
| | 480 | X − 27 | Y + 5 | 1:5 |
| | 720 | X − 32 | Y + 3 | 1:5 |
| | 960 | X − 35 | Y + 2 | 1:5 |
| | 1200 | X − 33 | Y + 6 | 1:5 |

X = 45% and Y = 50%

Here, X is % conversion of propane dehydrogenation to propylene using Mo—Sn/FAU catalyst and Y is % selectivity of propane dehydrogenation to propylene using Mo—Sn/FAU catalyst.

The main advantages of embodiments herein are:
1. The processes convert propane to propylene at a low temperature in a single step with a single bi-metallic catalyst.
2. The processes provide not only a good conversion but also an excellent yield of propylene in continuous process.
3. The processes run at atmospheric pressure to achieve 18-25% propylene yield at a temperature of 450° C., which is the major advantage of this process.

4. The employed catalyst does not contain any noble metal and comprises one metal from group VI B in combination with another metal from group III A or IV A which is the major advantage of the process.
5. The catalyst can be prepared easily and used in very low amounts (GHSV range of 5000-9000 h$^{-1}$); therefore, very economical to produce propylene.
6. The catalyst does not show major deactivation until 24 h of time-on-stream in a continuous process.

What is claimed is:

1. A catalyst composition comprising:
   (a) a porous alumina-silicate zeolite selected from the group consisting of Faujasite (FAU), Zeolite Mobil type Five (MFI), Zeolite Kerr Five (KFI) and Zeolite Beta polymorph A (BEA) as catalyst support;
   (b) a first metal selected from transition metals of group VIB, wherein the amount of the first metal is from 1 wt % to 10 wt % based on the porous alumina-silicate zeolite;
   (c) a second metal selected from metals of group IIIA or IVA, wherein the amount of the second metal is from 1 wt % to 8 wt % based on the porous alumina-silicate zeolite; and
   (d) an alkali metal, wherein the amount of alkali metal is from 0.5 wt % to 2 wt % based on the porous alumina-silicate zeolite,
   wherein the catalyst composition is free of noble metal.

2. The catalyst composition of claim 1, wherein the first metal is selected from the group consisting of molybdenum, chromium, and tungsten.

3. The catalyst composition of claim 1, wherein the second metal is selected from the group consisting of tin, gallium, and indium.

4. The catalyst composition of claim 1, wherein the alkali metal is selected from the group consisting of sodium, potassium, and cesium.

5. The catalyst composition of claim 1, wherein
   the first metal is selected from the group consisting of molybdenum, chromium, and tungsten;
   the second metal is selected from the group consisting of tin, gallium, and indium; and
   the alkali metal is selected from the group consisting of sodium, potassium, and cesium.

6. The catalyst composition of claim 1, wherein the amount of the first metal is from 6 wt % to 10 wt % based on the porous alumina-silicate zeolite.

7. The catalyst composition of claim 1, wherein the amount of the first metal is from 6 wt % to 8 wt % based on the porous alumina-silicate zeolite.

8. The catalyst composition of claim 1, consisting of the porous alumina-silicate zeolite of (a), the first metal of (b), the second metal of (c), and the alkali metal of (d).

9. The catalyst composition of claim 8, wherein:
   the first metal is selected from the group consisting of molybdenum, chromium, and tungsten;
   the second metal is selected from the group consisting of tin, gallium, and indium; and
   the alkali metal is selected from the group consisting of sodium, potassium, and cesium.

10. A process for preparing the catalyst composition according to claim 1, the process comprising:
    (a) depositing on a porous alumina-silicate zeolite a first metal selected from transition metals of group VIB, a second metal selected from metals of group IIIA or IVA, and an alkali metal, to obtain a catalyst precursor; and
    (b) exposing the catalyst precursor of (a) for calcination in an environment comprising air or nitrogen to obtain the catalyst composition,
    wherein the porous alumina-silicate zeolite is selected from the group consisting of FAU, MFI, KFI, and BEA.

11. The process of claim 10, wherein the first metal is selected from the group consisting of molybdenum, chromium, and tungsten.

12. The process of claim 10, wherein the second metal is selected from the group consisting of tin, gallium, and indium.

13. The process of claim 10, wherein the alkaline alkali metal is selected from the group consisting of sodium, potassium, and cesium.

14. The process of claim 10, wherein (a) further comprises:
    dissolving in water an ammonium salt, a nitrate salt, and a chloride salt of either one of the first metal selected from transition metals of group VIB to obtain a first solution, wherein the transition metal is selected from the group consisting of molybdenum, chromium, and tungsten;
    (ii) dissolving in water a nitrate salt and a chloride salt of either one of the second metal selected from group IIIA or IVA to obtain a second solution, wherein the second metal is selected from the group consisting of tin, gallium, and indium;
    (iii) mixing the first solution and the second solution, then adding addition cetyl trimethylammonium bromide (CTAB) with a weight ratio of the first and second metals to CTAB of 1:0.1 to 1:10, then aging for a time period from 1 hour to 2 hours;
    (iv) adding the porous alumina-silicate zeolite in the form of powder during the aging of (iii) to obtain a white slurry, wherein a temperature of the white slurry containing CTAB, zeolite, metal(s), and alkali metal is from 40° C. to 90° C.;
    (v) homogenizing the white slurry of (iv), then drying in an oven at a temperature from 100° C. to 150° C. for a time period from 10 hours to 18 hours to obtain a material; and
    (vi) calcining in air the material obtained in (v) at a temperature from 300° C. to 800° C. for a time period from 4 hours to 6 hours to obtain the catalyst precursor.

15. A continuous process for non-oxidative dehydrogenation of propane to propylene using the catalyst composition according to claim 1, the process comprising:
    (a) passing a mixture of propane and helium or nitrogen in a molar ratio of 1:5 to a reactor, in the absence or presence of hydrogen (1% 5%) in an amount of 1%-5% or steam in an amount of 1%-5%, wherein the reactor is kept at a pressure from 0.9 bar to 5 bar, a temperature from 350° C. to 700° C. with a gas hourly space velocity (GHSV) from 5000 h$^{-1}$ to 9000 h$^{-1}$ over the catalyst composition, for a time period from 1 hour to 24 hours to obtain a reaction product predominated with propylene.

16. The continuous process of claim 10, wherein the reaction product contains side products selected from methane, ethane, ethylene, or combination thereof.

17. The continuous process of claim 10, wherein the propane to propylene conversion is from 18% to 52% at a temperature of 450° C.

18. The continuous process of claim 10, wherein a yield of the propylene is from 10% to 25%.

* * * * *